(12) United States Patent
Izumori et al.

(10) Patent No.: US 8,748,589 B2
(45) Date of Patent: Jun. 10, 2014

(54) COMPLEX CRYSTALLINE SUGAR COMPRISING D-PSICOSE AND D-ALLOSE AND PROCESS FOR PRODUCTION OF THE SAME

(75) Inventors: Ken Izumori, Kagawa (JP); Masaaki Tokuda, Kagawa (JP); Goro Takata, Kagawa (JP); Kenji Morimoto, Kagawa (JP)

(73) Assignees: National University Corporation Kagawa University, Takamatsu-shi, Kagawa (JP); Matsutani Chemical Industry Co., Ltd., Itami-shi, Hyogo (JP)

( * ) Notice: Subject to any disclaimer, the term of this patent is extended or adjusted under 35 U.S.C. 154(b) by 1708 days.

(21) Appl. No.: 11/817,774

(22) PCT Filed: Mar. 3, 2006

(86) PCT No.: PCT/JP2006/304151
§ 371 (c)(1),
(2), (4) Date: Sep. 11, 2008

(87) PCT Pub. No.: WO2006/093292
PCT Pub. Date: Sep. 8, 2006

(65) Prior Publication Data
US 2009/0068710 A1    Mar. 12, 2009

(30) Foreign Application Priority Data

Mar. 4, 2005 (JP) .................................. 2005-61638

(51) Int. Cl.
*C07H 1/00* (2006.01)
(52) U.S. Cl.
USPC ........................................................ 536/1.11
(58) Field of Classification Search
CPC ...................................................... C07H 3/02
See application file for complete search history.

(56) References Cited

FOREIGN PATENT DOCUMENTS

| JP | 2001-011090 A | 1/2001 |
|---|---|---|
| JP | 2004-298106 A | 10/2004 |

OTHER PUBLICATIONS

Bhuiyan et al. J Fermentation and Bioengineering, 1998, vol. 85, pp. 539-541.*
Takeshita et al. J Biosci Bioeng, 2000, vol. 90, pp. 453-455.*
Menavuvu et al.; "Efficient Biosynthesis of D-Allose from D-Psicose by Cross-Linked Recombinant L-Rhamnose Isomerase: Separation of Product by Ethanol Crystallization"; Journal of Bioscience and Bioengineering, vol. 101, No. 4, (2006), pp. 340-345.
Bhuiyan et al., "D-Allose Production from D-Psicose Using Immobilized L-Rhamnose Isomerase", Journal of Fermentation and Bioengineering, 1998, vol. 85(5), pp. 539 to 541, full text.
International Search Report of PCT/JP2006/304151, date of mailing May 16, 2006.

* cited by examiner

*Primary Examiner* — Layla Bland
(74) *Attorney, Agent, or Firm* — Westerman, Hattori, Daniels & Adrian, LLP (57) ABSTRACT

A complex crystalline sugar comprising D-psicose and D-allose and a method for producing the same are disclosed. The compositional ratio between D-psicose and D-allose in the sugar is about 1:1 to 1:4. A process for producing a complex crystalline sugar comprising D-psicose and D-allose, the process comprising producing a complex crystalline sugar comprising D-psicose and D-allose from a sugar solution containing D-psicose and p-allose and collecting the complex crystalline sugar. The solvent of the sugar solution used in the production of the complex crystalline sugar is water or a mixture of water and ethanol. The sugar solution containing D-psicose and D-allose is produced by a process comprising reacting D-psicose with L-rhamnose isomerase to convert D-psicose into D-allose. The L-rhamnose isomerase is derived from a strain (IPOD FERM BP-08593) belonging to *Pseudomonas stutzeri*.

5 Claims, 9 Drawing Sheets

| Microscopic photograph | Shape and size of crystal |
|---|---|
| D-psicose and D-allose mixture(7:3)  | Rod-like<br><br>Thickness: 10～30 μm<br>Length : 500～3000 μm |
| D-psicose  | Rod-like<br><br>Thickness: 40～50 μm<br>Length : 250～300 μm |
| D-allose  | Rod-like<br><br>Thickness: 30～50 μm<br>Length : 500～800 μm |

Fig. 6

①Crystal added

②No crystal added

COMPLEX CRYSTALLINE SUGAR COMPRISING D-PSICOSE AND D-ALLOSE AND PROCESS FOR PRODUCTION OF THE SAME

TECHNICAL FIELD

The present invention relates to a complex crystalline sugar comprising D-psicose and D-allose and a process for producing the same.

BACKGROUND ART

Monosaccharide is a generic term for a hydrocarbon having a carbon chain of 3 or more carbon atoms, and in nature there are a number of monosaccharides as much as 40 or more species in a variety of forms including free forms or derivatives of metabolites or biosynthetic products as well as complex carbohydrates, oligo-saccharides or polysaccharides. Industrially most important monosaccharide is D-glucose, of which the process for production has been established on an industrial scale using a method of hydrolysis of starch with an enzyme such as amylase, and has been industrially most widely used in the fields of foods, cosmetics and pharmaceuticals in large quantities. Further, D-fructose which is produced by conversion of D-glucose with isomerase is an industrially important sugar. Other industrially applied process for production of some monosaccharides includes production of L-sorbose from sorbitol by an acetic acid bacterium, production of D-galactose from lactose by β-galactosidase, and production of D-xylose from xylan by acid hydrolysis. A large number of other monosaccharides are difficult to produce in industrially large quantities because of industrial and economical limitation in raw materials, generative reaction and yield, and they almost have not yet been utilized industrially.

The present inventors have paid attention to such expensive and rarely available monosaccharides and gave a name of rare sugars to these monosaccharides; and they have continued to assiduously study the generative reaction of rare sugars for a long period of years. The present inventors have conducted a study for development on monomeric rare sugars including both D-psicose and D-allose. They, as mentioned in the non-patent document 1, have developed a process for producing D-psicose directly from D-glucose in combination of an industrially used D-xylose isomerase with D-ketohexose 3-epimerase discovered by the inventors, and thus opened a new route to a process for the continuous production of D-psicose.

D-Psicose which is generally known to exist in molasses of sweet potatoes in small quantities, is one of industrially expected sugars, particularly in food industry, since it has a sweet taste of good quality similar to D-fructose and is best suited as hardly fermentative and low calorie sugar. That is, D-psicose draws attention as a sugar which does not promote the synthesis of fat and does not accumulate body fat, particularly intraperitoneal fat in comparison with monosaccharides such as D-glucose or D-fructose (non-patent document 2). Further, it has been reported that the available energy value of D-psicose is approximately zero (non-patent document 3).

Thus, based on their success in producing D-psicose, they have succeeded in large scale production of a rare sugar D-allose by isomerization of D-psicose using L-rhamnose isomerase. In this connection, the present inventors have discovered L-rhamnose isomerase (also referred to as "L-RhI") produced by Pseudomonas stutzeri LL-172 strain, and further elucidated that this enzyme works to catalyze the isomerization reaction of L-rhamnose to L-rhamnurose as well as L-rhamnurose to L-rhamnose. L-Rhamnose isomerase produced by Pseudomonas stutzeri LL-172 (IPOD FERM BP-08593) also acts on isomerization between D-allose and D-psicose, and thus this enzyme is capable of producing D-allose from D-psicose. In this situation, it is necessary to use an enzyme of the Pseudomonas stutzeri LL-172 origin in order to produce D-allose from D-psicose (patent document 1). Because of discovery of this enzyme, practical use of the reaction for production of rare sugars aimed by the present inventors took a great step forward; particularly, this was remarkable in production of D-allose from the substrate D-psicose on a large scale. Since it became apparent that this D-allose has various physiological activities, the research is rapidly developing. At present, it has become apparent that D-allose has an effect such as cancer cell inhibition or antioxidant effect important in a medical field (patent document 2).

The production of D-allose, however, includes the most expensive bottleneck step for separating D-allose from D-psicose during the course of production. In order to produce D-allose as a single product, the product contained in a mixture of sugar solutions formed due to the property of the enzyme has to be separated from the raw materials. In the reaction with L-rhamnose isomerase, D-psicose and D-allose reach to an equilibrium state of 7:3, from which mixture of sugar solutions D-allose is separated by column chromatography. Though this operation for separation is naturally required as an essential step for purification of a monomeric sugar, it is also true that the time and labor are required as the production scale of rare sugar becomes huge.

On the other hand, "sugar solution of grape sugar/fruit sugar" containing D-glucose and D-fructose has practically been used as a mixture of sugars at present. The sugar solution of grape sugar/fruit sugar has industrially produced as alternative sugar having a compositional ratio similar to ordinary sugar by converting approximately a half of D-glucose to D-fructose using xylose isomerase, and is commercialized as gum syrup for use in coffee or tea. The mixed sugar solution of D-glucose and D-fructose is difficult to crystallize and utilized in a liquid form not as crystals. This is considered because of very high solubility of D-fructose in water, requiring much time and labor and producing a disadvantage in production cost; thus, it has been utilized as such without crystallization. The name of isomerized sugar usually indicates a mixed sugar solution of D-glucose and D-fructose. This is owing to the reason that at present only the sugar solution produced by isomerization reaction of D-glucose as raw material with xylose isomerase has been industrially made fit for practical use.

Non-patent document 1: Journal of Fermentation and Bioengineering, 80, p 101, 1995
Non-patent document 2: Asia Pacific J. Clin. Nutr. 10, 233-237,
Non-patent document 3: J. Nutr. Sci. Vitaminol 48, 77-80, 2002
Patent document 1: PCT WO2004/063369 A1)
Patent document 2: PCT WO03/097820 A1

DISCLOSURE OF INVENTION

Problems to be Solved by the Invention

In this situation, if it is possible to obtain a mixture of crystals of both rare sugars, i.e., D-psicose and D-allose, from a mixture of both of sugar solutions after the reaction completion without any operation for separation, a new rare sugar mixture as crystals could be produced at low cost while making the best use of the physiological activities of the respective sugars; this is greatly expected industrially. That is, as an economically advantageous process for industrially producing sugars containing D-allose, it is strongly desired that a sugar solution containing D-psicose and D-allose is used as such without separating/purifying D-allose from the reaction mixture of L-RhI, and a crystalline sugar can be obtained from the sugar solution in high yield. In spite of such a situation, it was common knowledge that it could not be considered that in general a mixture of crystals could be obtained without separating D-allose from the reaction solution of L-rhamnose isomerase in the coexistence of D-psicose and D-allose, and thus, development research was so far conducted for monomeric rare sugar as a subject for both of D-psicose and D-allose.

The present inventors attempted to produce as a reagent a mixture of sugars in equilibrium from the L-RhI reaction.

That is, the object of the present invention is to establish a new process for recovering crystalline sugars from a sugar solution containing D-psicose and D-allose in high yield, and concurrently elucidate the characteristic feature of the crystalline sugars obtained by said process, and to provide a process for producing such crystalline sugars.

Means for Solving the Problems

A mixed sugar solution of D-psicose and D-allose obtained by the L-rhamnose isomerase reaction (L-RhI) is a product of isomerization, which product may be referred to as isomerized sugar.

The present inventors assiduously continued to study in order to obtain a crystalline sugar from a mixture containing D-psicose and D-allose obtained in high yield by the reaction of L-rhamnose isomerase (L-RhI).

In general, a mixture of sugars has an inferior property for crystallization. For example, a typical example is a mixed sugar solution of D-glucose and D-fructose, which has widely been used as a sweetener of isomerized sugar, wherein the property that a mixture of both sugars does not crystallize is utilized to use as a sweetener in a form of syrup. In such a situation, a mixture of rare sugars, D-psicose and D-allose, was accidentally obtained successfully for the first time without any expectation, since pure D-psicose and D-allose could be produced in an enough amount.

Consequently, the present inventors found that a quite new complex crystalline sugar was generated from a mixture containing D-psicose and D-allose, and that this was a new complex crystal in which the compositional ratio of D-psicose and D-allose in the crystalline sugar was about 1:1 to 1:4, and further they established a process for producing this complex crystalline sugar. Thus, the invention was completed.

That is, the above-mentioned problems in the present invention are dissolved by providing a complex crystalline sugar comprising D-psicose and D-allose and a process for producing a complex crystalline sugar which comprises generating a complex crystalline sugar comprising D-psicose and D-allose from a sugar solution containing D-psicose and D-allose, and recovering the same.

The invention is characterized by the following complex crystalline sugars (1) and (2).

(1) Complex crystalline sugar comprising D-psicose and D-allose.

(2) Complex crystalline sugar as described in (1), wherein the compositional ratio of D-psicose and D-allose contained in the complex crystalline sugar is about 1:1 to 1:4.

The invention is further characterized by the following process for producing a complex crystalline sugar as described in (3) to (6).

(3) A process for producing a complex crystalline sugar of (1) or (2) which comprises generating a complex crystalline sugar comprising D-psicose and D-allose from a sugar solution containing D-psicose and D-allose, and recovering the same.

(4) A process for producing a complex crystalline sugar as described in (3), wherein the solvent of the sugar solution used for generating the complex crystalline sugar is water, or a mixture of water and ethanol.

(5) A process for producing a complex crystalline sugar as described in (3) or (4), wherein the sugar solution containing D-psicose and D-allose is obtained by a process involving a step for converting D-psicose into D-allose by action of L-rhamnose isomerase.

(6) A process for producing a complex crystalline sugar as described in (5), wherein the L-rhamnose isomerase is derived from a strain (IPOD FERM BP-08593) belonging to *Psudomonas stutzerii*.

Effect of the Invention

The rare sugars, D-psicose and D-allose, respectively have a characteristic physiological activity, and their utility is greatly expected (patent document 2, etc.). D-Allose can be produced only by isomerizing D-psicose with L-rhamnose isomerase and separating D-allose from the isomerized mixture. In this invention, it became clear that D-psicose and D-allose can be obtained as mixed crystals without conducting any separation step, and accordingly this allows utility as a new material having concurrently two physiological activities and cost cutting since a step for separation is omitted.

In addition, this is quite effective as a process for producing pure sugar by purification by crystallization.

BEST MODE FOR CARRYING OUT THE INVENTION

The complex crystalline sugar comprising D-psicose and D-allose defined in this invention means those showing a crystal shape quite different from either crystals of D-psicose and D-allose in a powder X-ray diffractometry. The raw sugar used in the invention may be a mixed sugar containing D-psicose and D-allose, from which such a complex crystalline sugar can be produced.

In producing advantageously such a mixed sugar, D-psicose is subjected to the isomerization reaction with L-rhamnose isomerase to yield a mixture of D-psicose and D-allose.

In producing D-allose form D-psicose, an enzyme derived from *Pseudomonas stutzeri* LL172 (IPOD FERM BP-08593) is necessarily required (patent document 1).

The above-mentioned L-rhamnose isomerase is an enzyme having the following physical and chemical properties.

(a) Action

Figure 7:
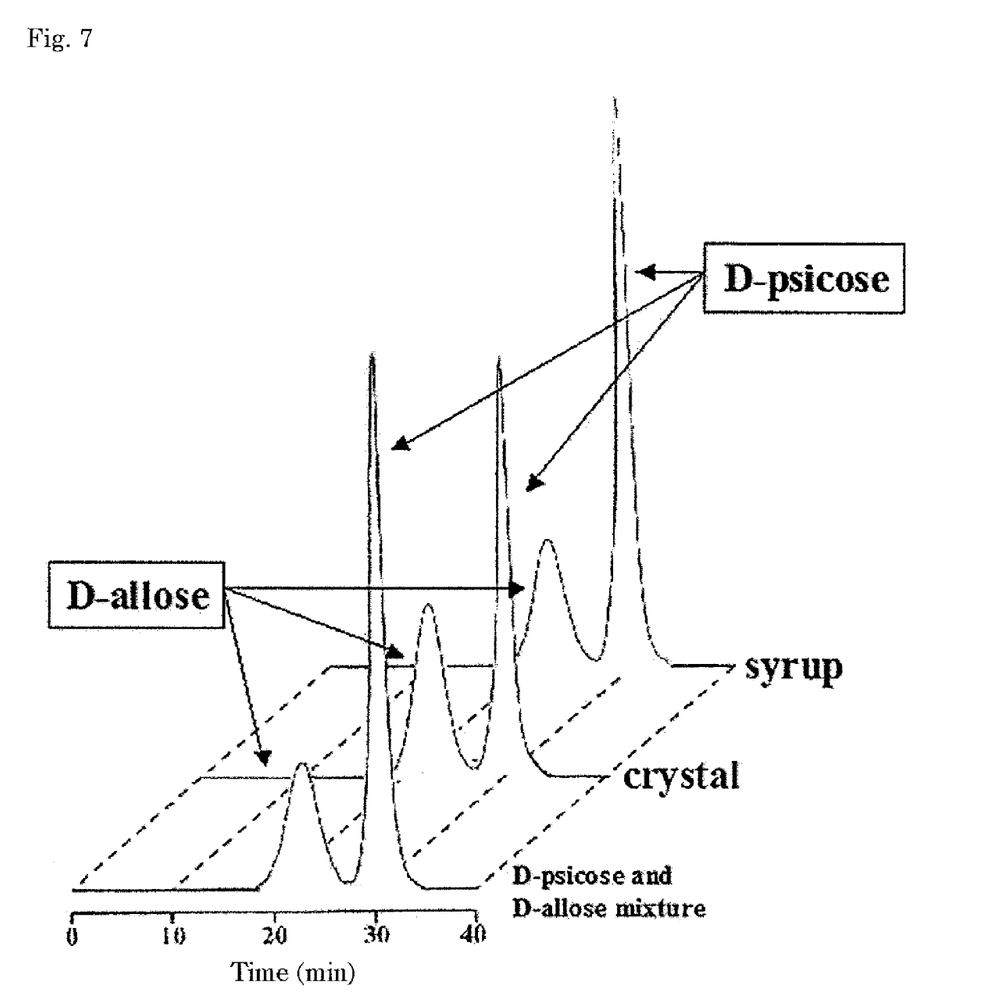
FIG. 7 shows the result of analysis of crystals by high performance liquid chromatography (D-psicose/D-allose=7:3).
Figure 8:
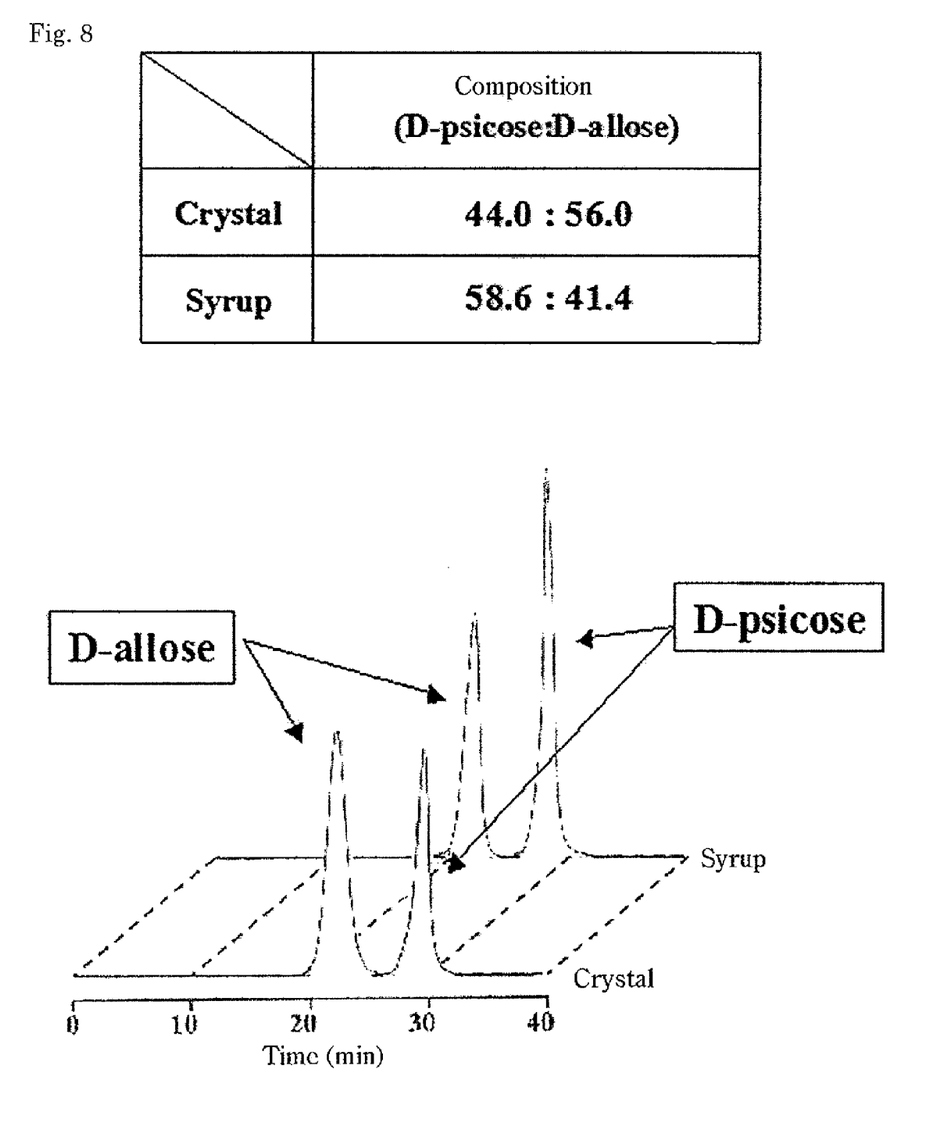
FIG. 8 shows the result of analysis of crystals by high performance liquid chromatography (D-psicose/D-allose=1:1).
Figure 9:
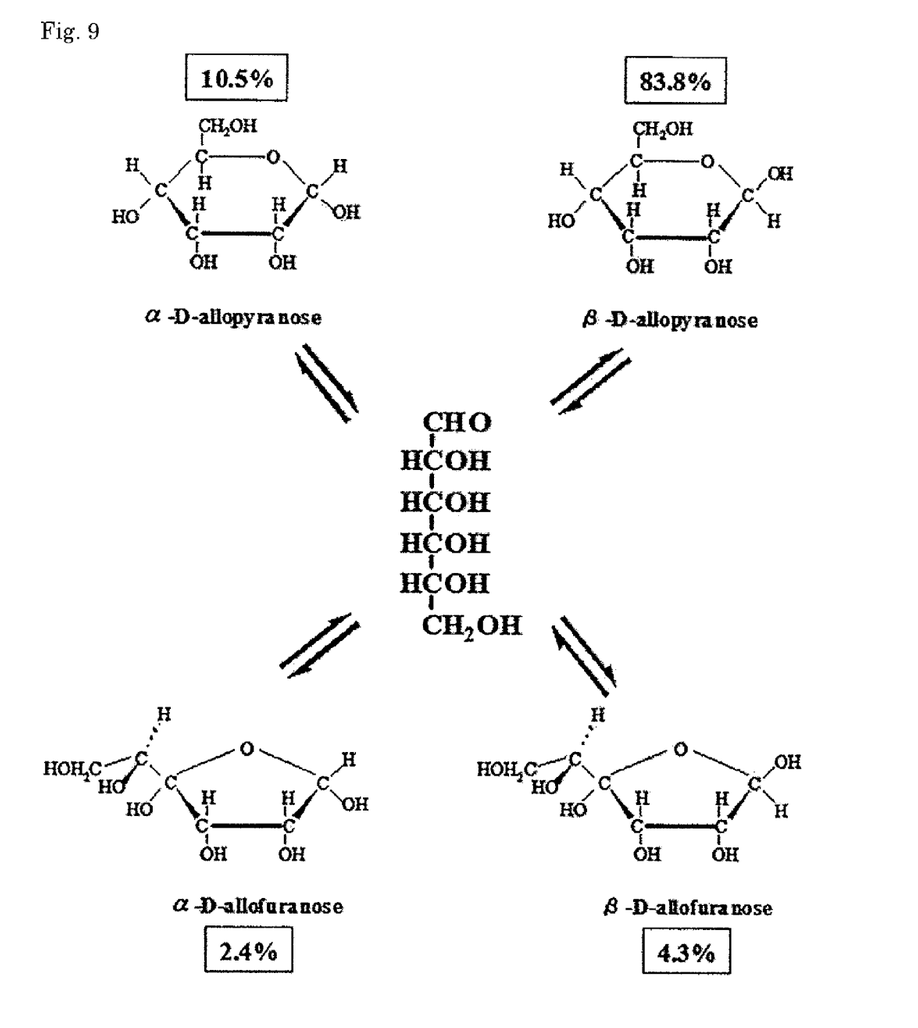
FIG. 9 shows the structure of a series of D-allose in a solution.

Catalyzing the isomerization reaction as indicated by bold lines in FIGS. 7, 8 and 9.

(b) Acting pH and Optimal pH

The acting pH is 7.0-10.0; and the optimal pH 9.0.

(c) pH Stability

When kept at 4° C. at a variety of pH for 1 hour, stable in the range of pH 6.0-11.0.

(d) Acting Temperature and Optimal Temperature

The acting temperature is 40-65° C., and the optimal temperature 60° C.

(e) Temperature Stability

Stable at 40° C. for 10 minutes, and at 50° C. for 10 minutes 90% or more remaining unchanged.

(f) Influence of a Chelating Agent

Almost no activity was inhibited by the coexistence of a chelating agent, EDTA or EGTA, at the time of measurement of the activity.

(g) Influence of Metal Ions

About 30% was inhibited by 1 mM cobalt ion.

(h) Molecular Weight Determined by an SDS-PAGE Method

Approximately 43,000.

The rate of D-psicose and D-allose in the prepared sugar is usually about 70% and about 30%, respectively, for the solid material. If necessary, it is optional to produce a mixed sugar of D-psicose and D-allose at this rate by making L-rhamnose isomerase act on D-psicose. Alternatively, it is also possible to produce a mixture of D-psicose and D-allose by isomerization of D-psicose with an inorganic and/or organic catalyst. In such a case, since the purity of D-allose is usually low, it is also possible to raise the purity of D-allose by addition of D-allose or by removal of D-psicose by fractionation with a solvent, separation with a membrane, fractionation with a column or treatment with an enzyme. Of course, the mixture of D-psicose and D-allose may be prepared by simply mixing D-psicose and D-allose at an optional rate.

In the invention, a complex crystalline sugar comprising D-psicose and D-allose may be produced by generating a complex crystalline sugar comprising D-psicose and D-allose from a sugar solution containing D-psicose and D-allose, and recovering the same.

The mixed sugar of D-psicose and D-allose, as mentioned in Example 1 below, forms crystals at 85% when the crystals were added at a specific concentration and at 90% or more when no crystal added. It is a characteristic feature of the mixed sugar of D-psicose and D-allose that it readily forms crystals without addition of the crystals. The crystal is in the shape of long and thin rod that is difficult to say similar to either crystal of D-psicose and D-allose. The monomeric D-allose is very easily crystallized, and when allowed to stand at about 60% concentration it yields crystals. D-Psicose is not to say readily crystallized, but it is at least better than D-fructose; this is considered to be a factor for relatively easy formation of crystals even in a state of mixed sugar. It was also confirmed that increase of the sugar concentration promotes the growth of the size of single crystal.

The composition of crystals confirmed by HPLC indicates that the content of D-allose therein is larger than that of D-psicose. D-Psicose and D-allose are not crystallized in the same rate as that before crystallization, similarly to a case of a mixed sugar of D-psicose and D-fructose. Though the content of D-allose in the solution before crystallization is equal to or less than 50% of that of D-psicose, the content of D-allose in the crystals is equivalent to or higher than that of D-psicose. On the other hand, when D-psicose and D-allose are mixed in the ratio of 1:1, the compositional ratio of D-psicose to D-allose in the resulting crystals becomes about 2:3, indicating that the content in the crystal is larger in D-allose. In other words, when a mixed sugar of D-psicose and D-allose is crystallized, it is considered that the crystal structure becomes stable in the ratio between 1:1 and 2:3 of D-psicose to D-allose.

Therefore, in the process for producing a complex crystalline sugar comprising D-psicose and D-allose, the sugar containing D-psicose and D-allose, or desirably a highly concentrated solution containing D-psicose and D-allose in the compositional ratio of about 1:1 to 2:3, or desirably an aqueous solution containing 70% to 95% (w/w) (hereinafter, "% (w/w)" is merely described as "%" unless otherwise stated) solid portion, is placed, for example, in a co-crystallization vessel, to which is added a proper amount (preferably, about 0.01 to 10%) of a complex crystalline sugar comprising D-psicose and D-allose as seed crystals; the mixture may be agitated, crystallized out, converted to massecuite, pulverized, and recovered. In this operation, a hydrophilic organic solvent such as ethanol may be added to the sugar solution containing D-psicose and D-allose in order to promote generation of the complex crystalline sugar comprising D-psicose and D-allose.

In the invention, the production of powder of the complex crystalline sugar from the massecuite may be achieved properly using, for example, spray drying, fluid granulation, block grinding, and the like. In spray drying, usually, massecuite, in which the content of solid portion is 70 to 85% and the crystallization rate of the complex crystalline sugar comprising D-psicose and D-allose is about 5 to 50%, may be sprayed from a nozzle with a high pressure pump and dried with hot air at a temperature at which the powdered sugar containing crystals are not melted, for example, 40 to 75° C., and then at 25 to 40° C., for about 1 to 24 hours, crystallized out, and aged. In block grinding, usually, massecuite, in which the content of solid portion is 85 to 95% and the crystallization rate of the complex crystalline sugar comprising D-psicose and D-allose is about 1 to 30%, may be allowed to stand for a period of about 1 to 10 days to totally crystallize out and solidify in a form of block, which then may be pulverized by grinding or cutting and dried.

Thus resulting powder of the complex crystalline sugar of the invention is easily handled since it has low hygroscopicity, does not solidify, and is good in fluidity compared to non-crystalline sugar. Thus, the physical and human cost required for envelopment, transportation, and management such as stock can be reduced greatly.

The complex crystalline sugar comprising D-psicose and D-allose of the invention comprises a mixture of D-psicose (which is expected to utilize as a non-calorie sweetener or physiologically functional food) and D-allose (which is recognized to have a cancer cell growth inhibiting action), and is expected to have a high utility value.

The invention will be explained in more detail by the following Examples, which are not intended to limit the invention in any way.

EXAMPLE 1

Production of a Mixed Sugar of D-Psicose and D-Allose with L-Rhamnose Isomerase The present inventors succeeded in large scale production of a rare sugar D-psicose. In Example 1, in anticipation of development of a new reagent, the production of another mixed rare sugar was attempted. The inventors have already been succeeded in large scale production of a rare sugar D-allose from D-psicose with L-rhamnose isomerase (see: JP-A 2004/298106 official gazette, etc.). In Example 1, a mixed sugar of D-psicose and D-allose was produced as another new isomerized sugar different from a monomeric D-psicose or D-allose.

[Experimental Method]

1) Reagents Used

Unless otherwise stated, the reagents and sugars used in the culture and enzymatic reaction in Example 1, similarly in the production of a rare sugar D-psicose, were obtained as the special grade from Wako Pure Chemical Industries, Ltd., and Nacalai Tesque, Inc.

2) Strain and Plasmid Used

*Escherichia coli* JM109 strain was used. Plasmid pOI-01 which was constructed by Ishimura in our laboratory by introducing an L-RhI gene of *Pseudomonas stutzeri* LL172 into an expression vector pQE60, was used. Table 1 shows the genotype of *Escherichia coli* JM109.

TABLE 1

| Genotype of *Escherichia coli* JM109 | |
|---|---|
| Strain | Description |
| *Escherichia coli* JM109 | E14-(McrA-), recA1, endA1, gyrA96, thi-1 hsdR17(rk-mk+), supE44, relA1, Δ(lac-proAB), [F'trad36, proAB, lacIqZΔM15] |

3) Composition of Medium

In culture of *Escherichia coli*, an LB agar medium was used as a plane medium, and a Super broth medium as a liquid medium. To each medium was added ampicillin at the final concentration of 100 μg/ml. Table 2 shows the composition of each medium.

TABLE 2

| The composition of medium for culturing *Escherichia coli* | |
|---|---|
| Super medium | |
| Bacto trypton | 3.5% |
| Bacto yeast extract | 2.0% |
| NaCl | 0.5% |
| LB medium | |
| Base for LB medium | 2.0% |

4) Transformation

According to the method of Cohen et al. (Cohen, S. N., Chang, A. C. Y. and Hsu, L. (1972) Proc. Natl. Acad. Sci. USA, 69, 2110), *Escherichia coli* JM109 was transformed as follows. To the competent cells of *Escherichia coli* JM109 was added 1 μl of plasmid pOI-01, and the mixture was allowed to stand in ice for 30 minutes, and then in a thermostatic bath at 42° C. for 90 seconds for giving heat shock, and then in ice for 2 minutes for giving cold shock. There was added 800 μl of SOC medium, which was shaken at 37° C. for 1 hour, and the mixture (2 μl) was plated on an LB medium containing ampicillin with a conradi stick and incubated at 28° C. overnight.

5) Incubation of a Recombinant *Escherichia coli*

Prepro-incubation and pre-incubation of the recombinant *Escherichia coli* was conducted in the following culture condition.

Prepro-incubation: A colony of the transformed *Escherichia coli* JM109 was scratched with a toothpick and inoculated on 3 ml of Super broth liquid medium containing 100 mg/ml of ampicillin and incubated at 28° C. with shaking for 12 hours.

Pre-incubation: The whole of the prepro-incubated culture broth was added to 100 ml of the same medium and incubated with shaking in the same condition as in the prepro-incubation.

This incubation was carried out in 10 L of culture medium, and a jar fermentor of 20 L in total volume was used. The whole of the culture broth of the pre-incubation was added thereto and incubated at 30° C. with shaking for 12 hours.

6) Induction of Enzyme with IPTG and Extraction of Crude Enzyme

After completion of the main culture, isopropyl thiogalactopyranoside (IPTG) was added so that the final concentration was 1 mM, and the mixture was stirred at 30° C. for 4 hours to induce enzyme. After termination of enzyme induction, the culture broth was centrifuged (9,000 rpm, 20 min, 4° C.) to collect the cells, which were washed with 50 mM glycine-NaOH buffer (pH9.0) to yield the cells. The resulting cells were crushed by an alumina grinding method. The ground cells were suspended into the same buffer, and centrifuged (12,000 rpm, 4° C., 30 min) to recover the supernatant as a crude enzyme solution.

7) Determination of the Activity of L-RhI

In determining the L-RhI activity, the enzyme reaction was conducted using D-allose as substrate, and the amount of D-psicose thus produced was determined. The enzyme reaction was conducted in the composition as shown in Table 3 (composition of the reaction solution for determining the L-rhamnose isomerase activity) at 30° C. for 10 minutes, and the reaction was stopped by addition of 50 μl of 10% trichloroacetic acid. In analysis of the sugar (ketose produced), a cysteine carbazole method was employed. The cysteine carbazole method as shown in Table 4 (a flow chart of determination by a cysteine carbazole method) was conducted by adding 0.1 ml of 0.5% cysteine solution and 3 ml of 70% sulfuric acid successively to 0.5 ml of a properly diluted sample, placing the mixture in water with stirring, and cooling. Then, 0.1 ml of 0.12% carbazole solution was added, stirred, and allowed to react at 35° C. for 20 minutes. After the reaction completion, the absorbance was measured at 540 nm by means of a spectrophotometer (JASCO, Ubest-30 UV/VIS Spectrophotometer) In this condition, the amount of enzyme producing 1 μmol/min of D-psicose was defined as 1 unit (U).

TABLE 3

| Reaction mixture for assay of L-rhamnose isomerase activity | |
|---|---|
| Enzyme | 50 μl |
| 0.05M L-Rhamnose | 50 μl |
| 0.05M Glycine-NaOH buffer (pH 9.0) | 350 μl |
| 0.01M MnCl$_2$ | 50 μl |

TABLE 3-continued

Reaction mixture for assay of L-rhamnose isomerase activity

| | |
|---|---|
| Total | 500 µl |
| | 30° C. 10 min |

TABLE 4

Flow chart of the cysteine carbazole method

Sample 0.5 ml
⟵ 1.5% Cysteine
⟵ 79% H$_2$SO$_4$
⟵ 0.12% Carbazole
↓
Thermal treatment
35° C., 20 min
↓
Abs 540 nm 8) Partial Purification of L-RhI by PEG#6000

To a crude enzyme solution was added an aqueous manganese chloride solution in small portions with stirring so that the final concentration was 10 mM. There was added PEG#6000 in small portion with stirring so that the final concentration was 10%, and the mixture stirred for 40 minutes. Then, the mixture was centrifuged (12,000 rpm, 30 min, 4° C.), and the supernatant was recovered. To this solution was added additionally PEG#6000 so that the final concentration was 20%, and the mixture was stirred for 40 minutes. The resulting precipitate was recovered by centrifugation (12,000 rpm, 30 min, 4° C.), and dissolved in 50 mM glycine-NaOH buffer (pH 9.0) to give a partially purified enzyme solution.

9) Immobilization of L-RhI

Anion exchange resin Chitopearl BCW2510 was used as a immobilization carrier as in immobilization of D-TE. Chitopearl resin was washed with 50 mM glycine-NaOH buffer (pH 9.0) and immersed in the same buffer with gentle agitation overnight for equilibration. Then, the buffer was removed, and the partially purified enzyme solution was added to the Chitopearl and stirred gently overnight for immobilization.

10) Production of a Mixed Sugar of D-Psicose and D-Allose

Using the immobilized enzyme, a mixed sugar of D-psicose and D-allose (7:3) was produced by a batch process. In a 500 mL conical flask was placed the immobilized enzyme, and 300 ml of 50% aqueous D-psicose solution was added. The flask was filled with nitrogen and the mixture was gently shaken at 45° C. for the enzyme reaction. After the D-psicose and D-allose reached an equilibrium state of 7:3, the reaction mixture was recovered, and further fresh 50% aqueous D-psicose solution was added. This operation was repeated until no enzyme activity was recognized.

11) Deionization Treatment

For deionization, a cation exchange resin (Dia-ion SKIB) and anion exchange resin (Amberlite IRA-411) were used. Both resins were mixed at an equal ratio and packed in a column, through which the solution after the reaction was passed to remove the ion.

12) Crystallization of a Mixed Sugar of D-Psicose and D-Allose

The mixed sugar solution thus produced was concentrated with an evaporator to 95% or higher, and the resulting syrup was moved into another vessel and allowed to stand at 28° C. for a day. Since the crystallization of the mixed sugar of D-psicose and D-allose was tried for the first time and no seed crystal available, the mixture was allowed to sand as such for crystallization in one experiment. In another experiment, a small amount of D-psicose powder was added, and the mixture was allowed to stand.

13) Pulverization of the Mixed Sugar of D-Psicose and D-Allose

The crystals were ground with a pestle and mortar into proper size and allowed stand in a drying room. After a lapse of one day, the crystals were again ground and placed in a drying room. This operation was repeated until the crystals of mixed sugar of D-psicose and D-allose gave powder.

[Results of Experiment]

1) Amount of the Recombinant *Escherichia coli* and the Enzyme Activity of L-RhI This time, the culture was conducted on 10 L scale to yield about 100 g of the recombinant *Escherichia coli*. The activity of crude enzyme L-RhI was about 5000 U/10 L for D-psicose. At present, we are conducting mass-production of D-allose with an immobilized enzyme having this enzyme activity; this indicates that mass-production of the mixed sugar of D-psicose and D-allose may be possible.

2) Production of a Mixed Sugar of D-Psicose and D-Allose from D-Psicose

Figure 1:
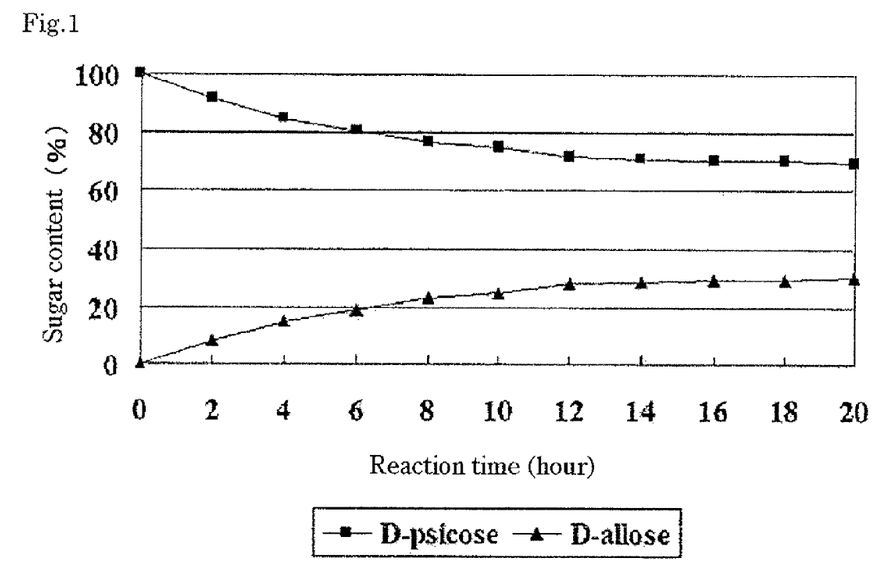
FIG. 1 shows the conversion of D-psicose into D-allose using an immobilized L-rhamnose isomerase.
Figure 2:
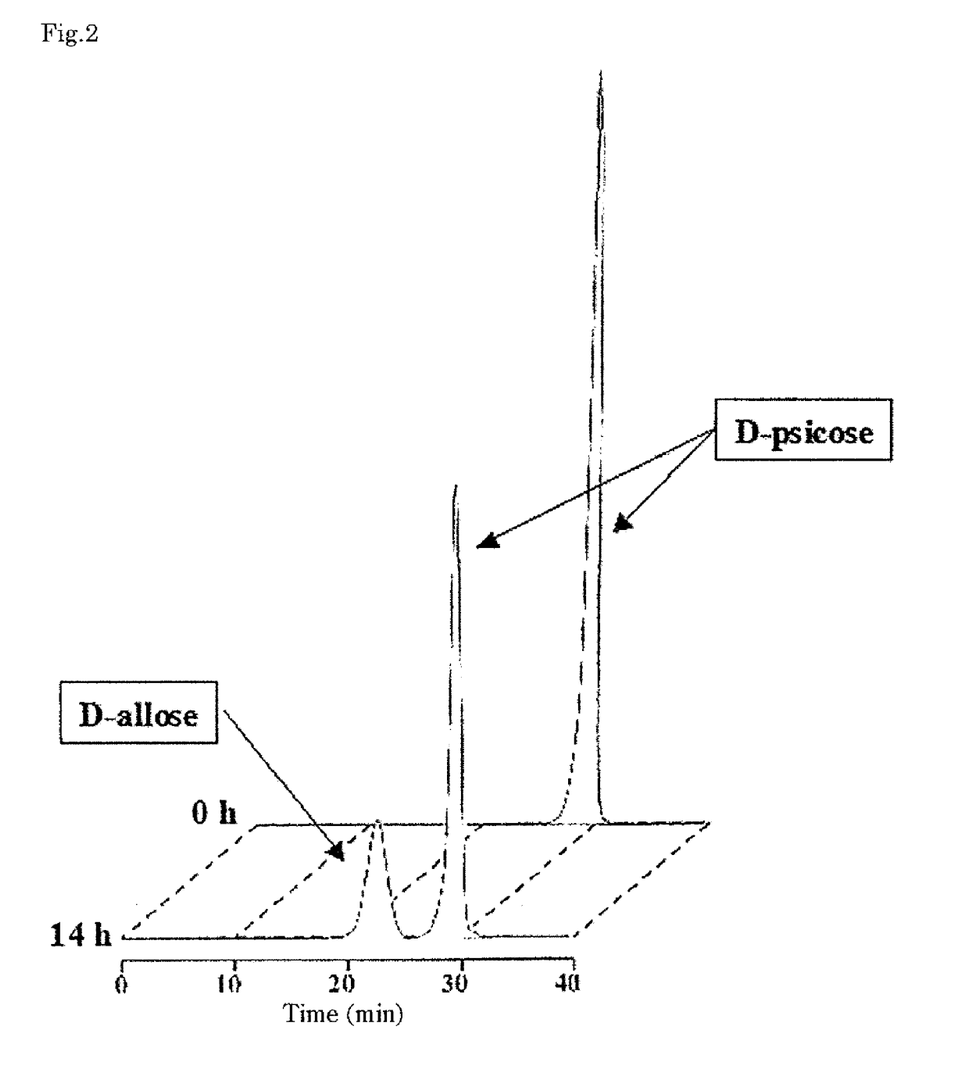
FIG. 2 shows the conversion of D-psicose into D-allose by the reaction with L-rhamnose isomerase, which was confirmed by high performance liquid chromatography.

This time, 50% aqueous D-psicose solution as substrate was allowed to react by a batch process, and the reaction was followed by sampling at proper times; the reaction reached the equilibrium of 7:3 between D-psicose and D-allose after about 14 hours (FIG. 1). In this situation, the reaction solution was changed every other day to produce the mixed sugar of D-psicose and D-allose (FIG. 2).

3) Crystallization and Pulverization of a Mixed Sugar of D-Psicose and D-Allose

For crystallization, a mixed sugar solution of D-psicose and D-allose was concentrated with an evaporator (EYELA Rotary Vacuum Evaporator N—N series) to 95% or higher sugar content, and the resulting syrup was moved into another vessel, and after seed crystals were added or nothing added, the solution was allowed to stand at room temperature. Since the crystallization of this mixed sugar was first trial this time, there was no crystal and no seed crystal available. In this situation, the crystals of a monomeric D-psicose were added in one case, and no crystal was added and left as such in another case; thus, the crystallization was tried for both cases. As a result, formation of crystals was observed in both cases, and the rate of crystallization was faster than the mixed sugar of D-psicose and D-allose.

Figure 3:
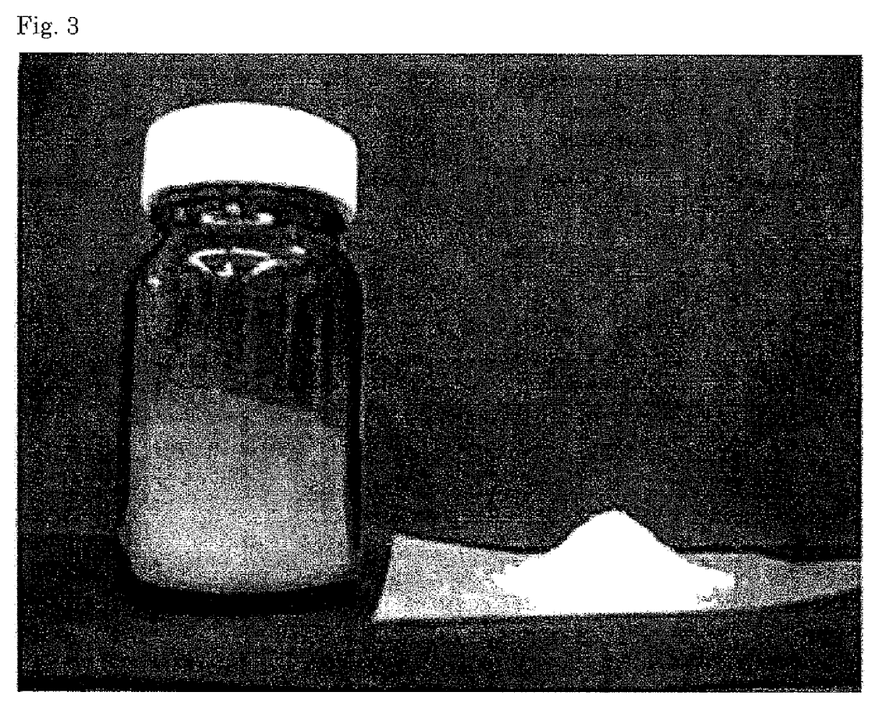
FIG. 3 shows a photograph of mixed crystals of D-psicose and D-allose produced by the reaction with an immobilized L-rhamnose isomerase.

Because water was sparingly used for crystallization, it was easy to make powder. Until now, it was succeeded in producing about 200 g of powdered crystals of the mixed sugar of D-psicose and D-allose (FIG. 3).

[Summary and Consideration]

*Escherichia coli* JM109 integrating a L-RhI gene was cultured in large quantities to yield a large amount of L-RhI. The enzyme was partially purified, immobilized on a resin for immobilization, and allowed to react with a substrate D-psicose to yield a mixed sugar of D-psicose and D-allose. This was concentrated with an evaporator to 95% sugar content, moved to a petri dish, and air-dried at 28° C. After a day, crystals begun to precipitate, and after 2 days the whole was crystallized. The resulting crystals were ground finely in a mortar to successfully yield powder. Thus, it was succeeded in producing about 200 g of powdered crystals until now. The crystals of this mixed sugar contained almost no water and could easily be pulverized. The ratio of D-psicose to D-allose in the mixed solution was 7:3, in which hardly crystallized D-psicose existed much more unexpectedly. This phenomenon is considered due to D-allose having a very easily crystallizing property greatly influenced on crystallization, or due to some synergistic effect for crystallization in combination of D-psicose and D-allose.

The big difference from the mixed sugar of D-psicose and D-fructose is that the mixed sugar of D-psicose and D-allose is very easily crystallized without adding any seed crystal. From this fact, it is considered that it can be utilized in a state of liquid, and even in a case of utilizing as crystallized solid it can effectively be crystallized.

The present inventors produce about 10 kg of D-allose a year. This indicates theoretically that in the case of mixed sugar it is possible to produce 3 times, i.e., about 30 kg per year. The mixture of D-psicose (which is expected to utilize as a non-calorie sweetener or physiologically functional food) and D-allose (which is recognized to have a cancer cell growth inhibiting action) is expected to have a high utility value.

EXAMPLE 2

Figure 4:
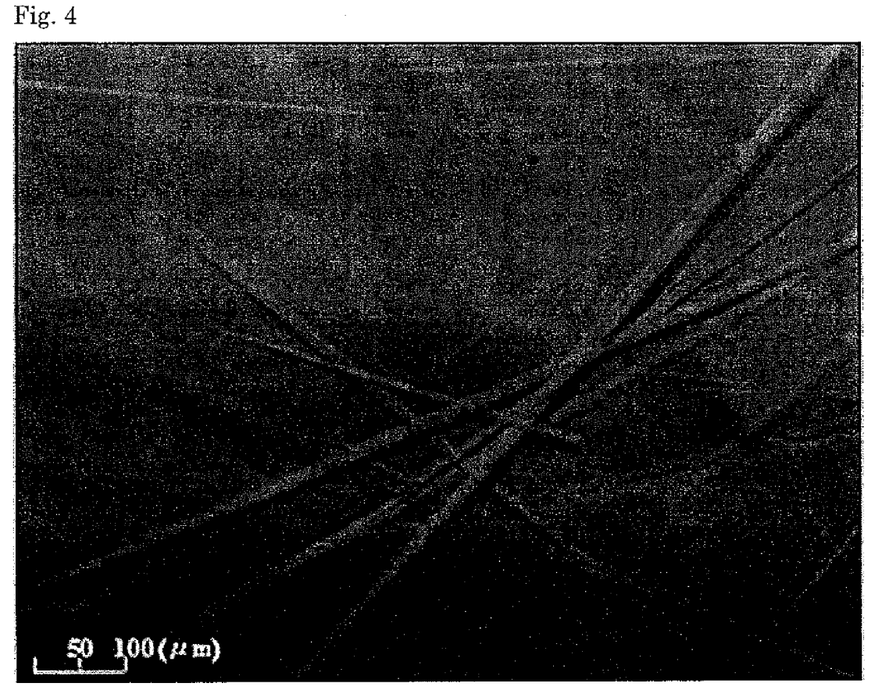
FIG. 4 shows a photograph of the crystals obtained from D-psicose and D-allose in the ratio of 7:3.
Figure 5:
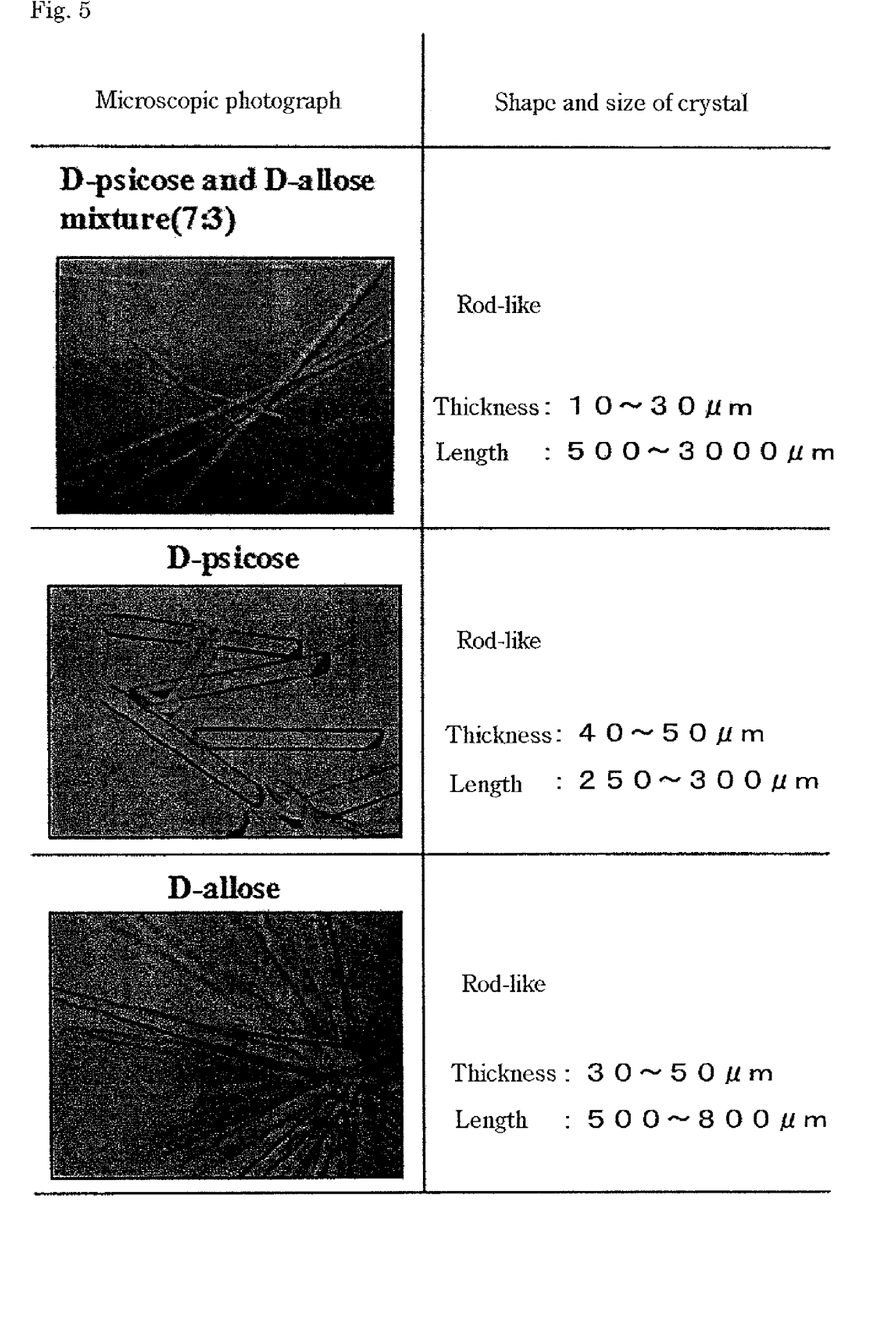
FIG. 5 shows comparison of each crystal form.
Figure 6:
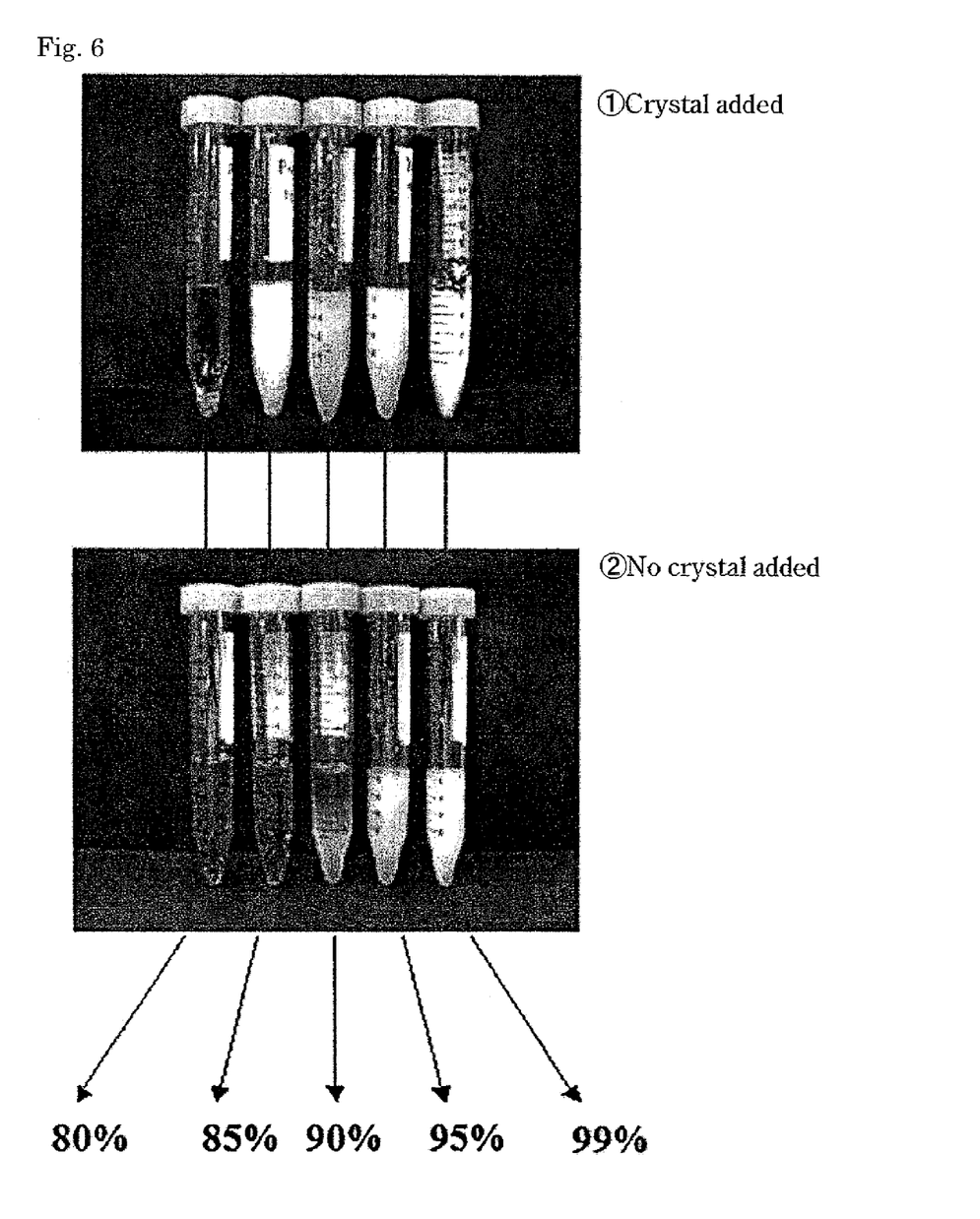
FIG. 6 shows an influence of the concentration in crystallization (at 28° C., for 24 hours).

Investigation of the Condition for Crystallization of a Mixed Sugar of D-Psicose and D-Allose In Example 2, in order to investigate what type of crystal component allows crystallization of the mixed sugar of D-psicose and D-allose, the crystal structure was analyzed, and in order to produce efficiently the mixed sugar of D-psicose and D-allose, an influence of the concentration and the difference of crystal structure were investigated, and the crystal composition was analyzed by HPLC.
[Experimental Method]
1) Reagents Used The mixed solution of D-psicose and D-allose used in this investigation was prepared in Example 1. The monomeric D-psicose and D-allose produced in our laboratory were used.
2) Observation of the Crystal Shape of the Mixed Sugar of D-Psicose and D-Allose An aqueous solution of the mixed sugar of D-psicose and D-allose thus prepared was concentrated to 98% with an evaporator, and the resulting syrup (about 20 ml) was moved into a petri dish. The moved syrup was allowed to stand as such at 28° C. without adding any crystal powder as seed. One day after standing, the crystals of the crystallized mixed sugar were observed by means of a stereoscopic microscope. In order to compare this crystal shape with those of the respective monomeric D-psicose and D-allose, the powders of D-psicose and D-allose were, respectively dissolved in water and then crystallized in the same manner, and the respective crystal shapes were observed by a microscope.
3) Influence of the Concentration on Crystallization The mixed sugar solution was concentrated to limit with an evaporator, and the resulting syrup was divided each 20 ml into five 25 ml corning tubes, to which was added water so that the concentrations respectively became 95%, 90%, and 80% (g/g) and the mixtures were stirred well for homogenization. Then, crystal powder as seed was added to one, and no crystal powder added to the other, and the both were allowed to stand at 28° C. for a day to compare the growth of crystals.
4) Analysis of the Sugar Composition in the Mixed Sugar Crystals of D-Psicose and D-Allose by HPLC Syrup of 90% sugar content containing mixed sugar of D-psicose and D-allose was placed in a Corning tube, to which was added a small amount of crystals as seed, and the mixture was allowed to stand at 28° C. with stirring. Before the syrup was totally crystallized, the crystals were separated by filtration under suction. The syrup and the crystals were respectively dissolved in water and applied to HPLC to compare the composition of the syrup with that of the crystals. On the other hand, a 1:1 mixture of D-psicose and D-allose was crystallized in the same condition, and the composition of the separated crystals were analyzed by HPLC and compared with those of 7:3.
[Results of Experiment]
1) Crystal Shape of the Mixed Sugar of D-Psicose and D-Allose The crystals of the mixed sugar of D-psicose and D-allose were observed by means of a microscope; as a result, a rod-like single crystal was observed as shown in FIG. 4. In addition, as shown in FIG. 5, the crystal shape obtained in D-psicose to D-allose 7:3 was rod-like (10-30 μm in thickness, 500-3000 μm in length); when compared structurally to those of monomeric D-psicose (rod-like, 40-50 μm in thickness, 250-300 μm in length) and D-allose (rod-like, 30-50 μm in thickness, 500-800 μm in length), both were different in their shape, indicating the possibility that the crystals were not formed by only one sugar. The crystals of the mixed sugar of D-psicose and D-allose grew with a lapse of time, which shape was visible to the naked eye. At present, crystallization is being tried to obtain a larger single crystal in order to conduct an analysis of crystal structure by X-ray on this crystal in the future.
2) Comparison of the Crystals of the Mixed Sugar of D-Psicose and D-Allose with those of D-Psicose and D-Allose FIG. 5 shows together microscopic photographs of the respective crystals and the actually measured crystal size. The crystals of the mixed sugar of D-psicose and D-allose, as mentioned above, have a long and thin rod-like shape, which is 10-30 μm across and 3 mm in length if it's long; in comparison to that of D-psicose or D-allose, it is not so broad in width and slender in length. This suggests that the crystal of the mixed sugar of D-psicose and D-allose is not single crystal of D-psicose or D-allose but mixed crystal.
3) Influence of the Concentration on Crystallization As mentioned above, the mixed sugar of D-psicose and D-allose can be crystallized without adding seed crystals. Thus, the influence of the concentration on crystallization was specifically investigated, and it was found that the crystallization was observed in standing as such at 90% or higher (FIG. 6 (2)). When the crystal was added, the crystallization occurred at the lower concentration of 85% (FIG. 6 (1)).
4) Composition of the Crystals by HPLC Syrup of the mixed sugar of D-psicose and D-allose was allowed to stand for a day, and the solution containing mixed crystals was filtered under suction to separate the crystal portion from the solution. These 2 samples and the solution before crystallization were respectively diluted with ion-exchange water so as to be 4% and analyzed by HPLC. The crystal composition of D-psicose and D-allose in the mixed sugar was in the ratio of about 1:1 to 3:4 (FIG. 7). Though in the solution the ratio was 7:3 and the rate of D-psicose was larger, the crystals contained a larger amount of D-allose. On the other hand, the crystals of the mixed sugar of D-psicose and D-allose in 1:1 were analyzed by HPLC, showing the same trend that the ratio of D-psicose to D-allose was approximately 2:3 (FIG. 8).
[Summary and Consideration]

It was confirmed that the crystal shape of the mixed sugar of D-psicose and D-allose is of long and thin rod-like crystal, which is 10-30 μm across and 500 μm-3000 μm in length and one kind of single crystal. The crystal shape was different from that of a monomeric D-psicose or D-allose. This supposedly indicates the possibility that the crystal of the mixed sugar of D-psicose and D-allose is not a single crystal of D-psicose or D-allose but mixed crystal.

It has been mentioned in Example 1 that the mixed sugar of D-psicose and D-allose is rapidly crystallized in contrast with psico-rare sugars, and specifically the concentration for crystallization was 85% when a crystal was added, and 90% or higher when no crystal was added. The greatest difference from the psico-rare sugars is that the mixed sugar of D-psicose and D-allose is very easily crystallized without adding any crystal as seed. The shape of the crystal is of a long and thin rod-like crystal, which can hardly be said to resemble either of D-psicose or D-allose. The monomeric D-allose has a very easily crystallizing property and thus it is easily crystallized on standing at the concentration of approximately 60%. D-Psicose cannot be said easily crystallized but its crystallinity is better than D-fructose, and accordingly it is considered that such a factor induces relatively easy crystallization even in the mixed sugar. Since it has also been confirmed that the higher sugar content promotes the growth of larger single crystal, we are now trying isolation of single crystal for use in X-ray crystal structure analysis.

In confirmation of the crystal composition by HPLC, it was found that the composition of D-psicose and D-allose contains a larger quantity of D-allose. The ratio of the sugars in the crystals was not the same as before crystallization as observed in the mixed sugar of D-psicose and D-fructose. Though the rate of D-allose in the solution before crystallization is 50% or lower than that of D-psicose, D-allose in the crystal is equivalent to or larger than D-psicose. On the other hand, the ratio of D-psicose to D-allose in the crystal composition becomes about 2:3 and the content of D-allose is slightly higher even if D-psicose and D-allose are initially mixed in the ratio of 1:1. Thus, it is considered that, when the mixed sugar of D-psicose and D-allose is crystallized, the crystal structure consisting of D-psicose and D-allose becomes stable in the ratio of about 1:1 to 2:3.

INDUSTRIAL APPLICABILITY

When there is great difference in a physical property such as solubility in the sugars existing in a mixture, the factor involved in the crystal sugar composition is considered to significantly depend on the physical property. Further, the factors such as the rate of crystallization influenced by the concentration and temperature or the equilibrium state between the structural isomers of sugar in aqueous solutions, are locked together complicatedly to form crystals. At present, the equilibrium of the structural isomers of D-allose in an aqueous solution has been elucidated together with D-psicose (FIG. 9). Though there are many unclear problems in crystallization of the mixed sugar solution, analysis of the crystal structure and research of the physical and chemical properties of rare sugars such as solubility are well under way recently, and a variety of physical properties of rare sugars are elucidated. Thus, research of the crystals of mixed sugars is expected to further advance in future.

The invention claimed is:

1. Complex crystalline sugar being a long and thin rod-like crystal in which the compositional ratio of D-psicose to D-allose is about 1:1 to 2:3.

2. A process for producing a complex crystalline sugar of claim 1, the method comprising:
   providing a sugar solution containing D-psicose and D-allose,
   generating a complex crystalline sugar comprising D-psicose and D-allose as a long and thin rod-like crystal different in shape from the monomeric D-psicose or D-allose from the sugar solution containing D-psicose and D-allose, and
   recovering the long and thin rod-like crystal.

3. A process for producing a complex crystalline sugar as claimed in claim 2, wherein a solvent of the sugar solution used for generating the complex crystalline sugar is water, or a mixture of water and ethanol.

4. A process for producing a complex crystalline sugar as claimed in claim 2, wherein the sugar solution containing D-psicose and D-allose is provided by converting D-psicose into D-allose by a reaction with L-rhamnose isomerase.

5. A process for producing a complex crystalline sugar as claimed in claim 4, wherein the L-rhamnose isomerase is derived from a strain (IPOD FERM BP-08593) belonging to *Psudomonas stutzeri*.

* * * * *